(12) United States Patent
Stergiopulos et al.

(10) Patent No.: US 8,080,002 B2
(45) Date of Patent: Dec. 20, 2011

(54) IMPLANTABLE DRUG DELIVERY DEVICE

(75) Inventors: Nikolaos Stergiopulos, Préverenges (CH); Michel Bachmann, Vaux-sur-Morges (CH)

(73) Assignee: Ecole Polytechnique Federale de Lausanne (EPFL), Lausanne (CH)

(*) Notice: Subject to any disclaimer, the term of this patent is extended or adjusted under 35 U.S.C. 154(b) by 136 days.

(21) Appl. No.: 12/377,011

(22) PCT Filed: Aug. 18, 2006

(86) PCT No.: PCT/IB2006/052864
§ 371 (c)(1),
(2), (4) Date: Feb. 10, 2009

(87) PCT Pub. No.: WO2008/020272
PCT Pub. Date: Feb. 21, 2008

(65) Prior Publication Data
US 2010/0168673 A1    Jul. 1, 2010

(51) Int. Cl.
*A61K 9/22* (2006.01)
*A61M 1/00* (2006.01)
*A61M 31/00* (2006.01)
*A61M 37/00* (2006.01)

(52) U.S. Cl. .......... 604/891.1; 604/93.01; 604/153
(58) Field of Classification Search .......... 604/154, 604/891.1, 502, 93.01, 131, 288.01–288.04
See application file for complete search history.

(56) References Cited

U.S. PATENT DOCUMENTS 4,525,164 A * 6/1985 Loeb et al. .......... 604/131
2005/0229683 A1* 10/2005 Ludin et al. .......... 73/40

FOREIGN PATENT DOCUMENTS

| CH | 688 224 | 6/1997 |
| WO | WO 96/41080 | 12/1996 |
| WO | WO 2004/012806 | 2/2004 |
| WO | WO 2005/077450 | 8/2005 |

OTHER PUBLICATIONS

International Search Report for PCT/IB2006/052864, mailed Jul. 31, 2007.
Written Opinion of the International Searching Authority for PCT/IB2006/052864, mailed Jul. 31, 2007.

* cited by examiner

*Primary Examiner* — Nicholas Lucchesi
*Assistant Examiner* — Rebecca E Eisenberg
(74) *Attorney, Agent, or Firm* — Nixon & Vanderhye P.C.

(57) ABSTRACT

The implantable drug delivery device comprises at least an implantable pump, a reservoir and a delivery chamber.

29 Claims, 9 Drawing Sheets

IMPLANTABLE DRUG DELIVERY DEVICE

This application is the U.S. national phase of International Application No. PCT/IB2006/052864, filed 18 Aug. 2006, which designated the U.S., the entire contents of which is hereby incorporated by reference.

TECHNICAL FIELD

The present invention generally relates to an implantable device.

More specifically, the present invention relates to a high-precision implantable drug delivery device with reservoir means.

BACKGROUND OF THE INVENTION

Peripheral vascular disease (PVD) results from the development of atherosclerosis, which in the lower limbs leads to poor circulation and poor perfusion of leg tissues, a condition called critical limb ischemia (CLI). In severe forms CLI manifests itself with leg pain, inability to walk, ischemic ulcers in the feet and toes, arterial emboli, and, at advanced stage, gangrene. Risk factors include smoking, diabetes, obesity, high blood cholesterol, a diet high in fats, and having a personal or family history of heart disease. In the United States the prevalence of peripheral vascular disease is 3%, with the prevalence of diabetes-induced PVD rising to 2.8%. About 82,000 non-traumatic lower-limb amputations are performed each year among people with diabetes. Clearly, solutions improving the conditions and treatments options for CLI are in need, especially in view of the ever increasing incidents of diabetes-related PVD.

The progression of PVD may be stopped if sufficient blood flow runs through the diseased vessels. Increase in blood flow can be achieved through exercise, which has been shown to be beneficiary to the outcome of disease. Alternatively, blood flow may be increased by continuous or periodical administration of drugs into the blood stream certain drugs that will act either locally or at the distal bed. This can be achieved by the intra-arterial release of angiogenetic or vasodilatatory substances.

Implantable medical devices suitable for the delivery of drug are known per se in the art. Swiss patent N° 688 224 discloses an implantable device for the delivery of liquid pharmaceutical drugs in the human body. Other examples of similar devices are disclosed in US 2004/0249365, WO 02/08233, WO 02/083207, DE 4123091, WO 03/089034, GB 2174218 and WO 96/41080, all incorporated by reference in the present application.

In the above-mentioned Swiss patent N° 688 224, the disclosed device comprises an axial piston pump. The piston is driven under control in rotation and axial translation. A fluid reservoir is connected to a suction side of the pump. The pump preferably has a ceramic cylinder and piston. A refilling connection for the reservoir is re-sealable. The integral rotary drive has a separate control unit. Pump, reservoir and drive are coaxial in a cylindrical casing. Alternatively the drive is external, a non-contact coupling transmitting rotary motion to the piston. The end face of the cylinder has a cam profile. An eccentric cam follower peg, which produces the axial motion, is attached to the piston. This system is rather complicated as it involves at least two displacements of the piston, i.e. a rotation coupled to a translation. According to this geometry, it is necessary to use specific means to transform the rotation created by the motor into a translation. The disclosed means complicate the construction, are a dysfunction risk and consume energy.

Another prior art pump is known from US patent application 2004/0044332. This publication discloses an implantable device for delivering medicines in liquid form comprising: a reservoir provided with an inlet and an outlet, said reservoir being adapted to expel the liquid; a variable volume chamber provided with an inlet and an outlet, the volume of the variable volume chamber being in particular smaller than that of the reservoir; a first conduit communicating the outlet of the reservoir with the inlet of the variable volume chamber to fill the latter; a second conduit whereof one of the ends is connected on the outlet of the variable volume chamber.

In this prior art, in fact two variable volume chambers are used (one being the reservoir), separated by a valve, and function by using their respective restoring forces to expel a desired quantity of liquid (for example medicine).

SUMMARY OF THE INVENTION

Accordingly, it is an aim of the invention to improve the known devices and methods.

It is also an aim of the present invention to provide a simple implantable device that is reliable.

Another aim of the present invention is to provide a system that allows a better dosage of the expelled liquid.

A further aim of the invention is to provide a system of small size allowing small animal research and laparoscopic implantation.

It is also an aim of the present invention to provide a reservoir suitable for use with the present pump.

These aims are achieved thanks to the apparatus defined in the claims.

The result is a promising solution, in which the idea is to infuse the specific drugs directly into an artery, the intrathecal space, intracranially or any other body location using a high-precision, telemetrically controlled, implantable intra-arterial drug infusion device. A high-concentration drug is stored within the implant and the dosing is low so that drug delivery can take place over long periods (weeks to months or years). Alternative designs may incorporate access ports for transcutaneous drug refill. Because the drugs are administered locally with non-systemic effects, the technology probes for a user-defined, low-dosage, high-precision and high efficiency drug delivery system.

Other advantages of the present invention include:
1. Small compact size to facilitate peripheral implantation, intracranial implantation, cardiac applications, laparoscopic insertion and small animal research.
2. High-precision bolus administration
3. Dosing independent of load (i.e., arterial pressure or intracranial pressure at distal end of delivery catheter)
4. Externally programmable/activated for continuous, periodic or user-defined drug administration
5. MRI safe and compatible.

Advantageous embodiments of the invention are the subject-matter of the dependent claims.

BRIEF DESCRIPTION OF THE DRAWINGS

Other features and advantages of the present invention will appear more clearly from reading the following detailed description of embodiments of the invention which are presented solely by way of non-restrictive examples and illustrated by the attached drawings in which:

FIGS. 1A to 1H show detailed cut views of the invention according to a first embodiment;

FIG. 2A to 2H show detailed cut views of the invention according to a second embodiment; and FIGS. 3 to 7 show detailed views of the invention according to a third embodiment.

DETAILED EMBODIMENTS OF THE INVENTION

Figure 1A:
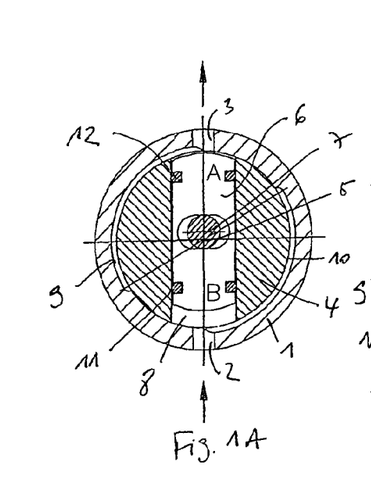

FIG. 1A shows a transverse cut view of a first embodiment of the pump according to the invention.

The pump comprises an external body 1 with an inlet 2 and an outlet 3. Said inlet 2 and said outlet 3 are connected, in a known fashion for example as disclosed in US 2004/0044332 to conduits or catheters in order to transfer liquid (for example a drug) from a reservoir to the site to be treated. These conduits are not represented in FIG. 1 for the sake of simplicity but are similar to the conduits disclosed in the US publication mentioned above. A more detailed description of examples of such catheters is given with reference to FIGS. 9A, to 9C and 10A to 10D in the present application.

Inside the body 1, there is a cylinder 4 rotating around a cylinder axis 5. Inside the cylinder 4, there is further a piston 6 which is driven in rotation by the cylinder 4 and which is rotated around a piston axis 7. The axis 7 is eccentric with respect to the axis 5 thus causing the piston 6 to move laterally inside the cylinder 4 when said cylinder is rotating.

In the body 1, the inlet 2 ends into an inlet chamber 8, which has a variable volume. This chamber 8, in this embodiment, is defined mainly by the relative position of the piston 6 in the cylinder 4 and inside wall of the body 1.

The system comprises in addition first and second temporary chambers 9 and 10 the use of which will be explained further below.

Finally, to maintain the sealing, the piston 6 carries two seals 11 and 12, for example O-rings.

Figures 1B, 1C:
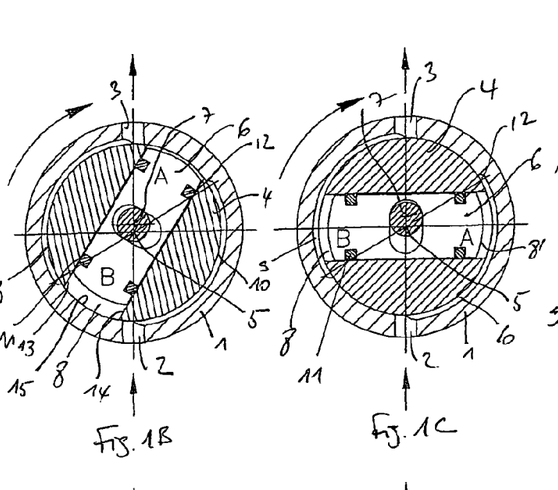

In FIG. 1B, the system is shown with the cylinder 4 and piston 6 rotated from about 30° clockwise relatively to the external body 1. In this position, the chamber 8 is now closed, i.e. is not linked anymore with inlet 2, and the volume 8 is defined by the end B of the piston 6, the inner walls 13, 14 of the cylinder 4 and the inner wall 15 of the external body 1.

In FIG. 1C, the cylinder 4 and piston 6 are further rotated from about 90° clockwise (value taken from the position of FIG. 1A) relatively to the external body 1. In this position, due to the fact that cylinder 4 and piston 6 rotate around axes which are eccentric with respect to each other, the piston 6 moves laterally with respect to the cylinder 4 thus reducing the volume of the chamber 8. At the same time, once cylinder and piston have left the position illustrated in FIG. 1B, the chamber 8 is linked to the temporary chamber 9 and by way of consequence to outlet 3. Accordingly, the liquid present in the chamber 8 is expelled through outlet 3 by the relative motion of the piston 6 in the cylinder 4.

At the same time, as can be seen on the right hand side of FIG. 1C, an inlet chamber 8' has been created on the side A of the piston 6 by its lateral movement relatively to the cylinder 4, this chamber 8' being connected to the second temporary chamber 10 and to inlet 2.

Figure 1D:
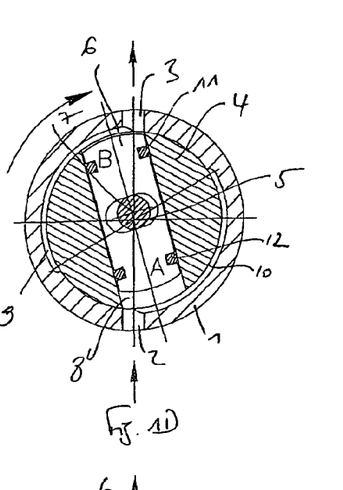

Further rotation of the cylinder 4 and piston 6 relatively to the external body 1 as illustrated in FIG. 1D shows that chamber 8 is finally totally suppressed be the displacement of piston 6 but at the same time the displacement creates another chamber 8' at the end A of the piston 6, the displacement of the piston 4 to form chamber 8' creating at the same time a suction force to fill chamber 8'.

Figure 1E:
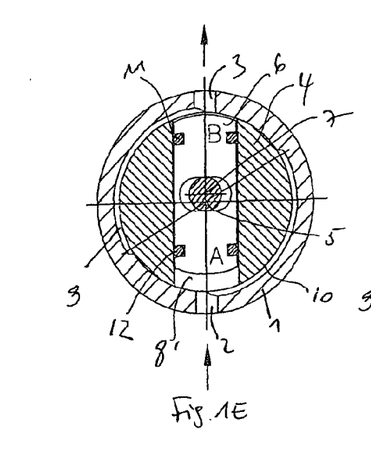

After a rotation of 180° clockwise of piston 6 and cylinder 4 from the position represented in FIG. 1A, the system is in the position represented in FIG. 1E, with the ends A and B of the piston 6 in inverted positions.

Figure 1F:
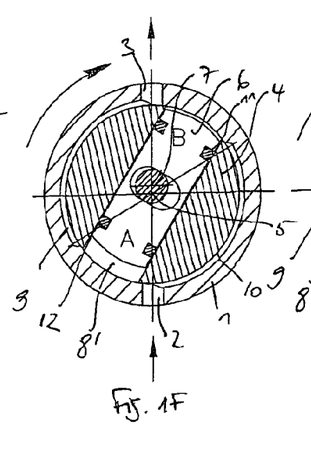
Figure 1H:
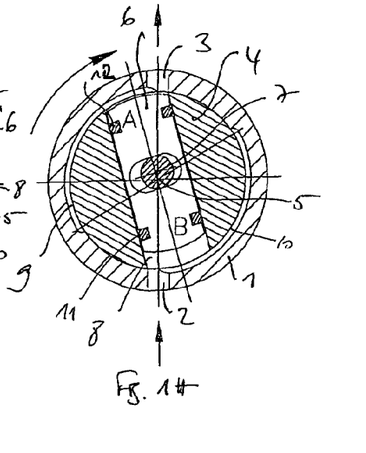

FIG. 1F to 1H show exactly the same movement of the system as represented in FIGS. 1A to 1D and the explanations given above apply correspondingly. Finally after the situation represented in FIG. 1H, further clockwise rotation of the piston 6 and cylinder 4 ends in the position represented in FIG. 1A and the cycle starts again.

As can be readily understood from the above description, the system allows to form a variable volume chamber (8 or 8') by the use of a piston and an eccentric system which transforms a pure rotation motion into a combination of rotation and lateral relative displacement.

FIGS. 2A to 2H show a second embodiment of the system of body, cylinder and piston. In this case, no eccentric axes (as the axis 5 and 7 of the first embodiment) are used but the system uses a pressure differential. More precisely, it uses the principle according to which the pressure of the liquid (for example a drug) is higher at the inlet than at the outlet.

Figures 2A, 2B:
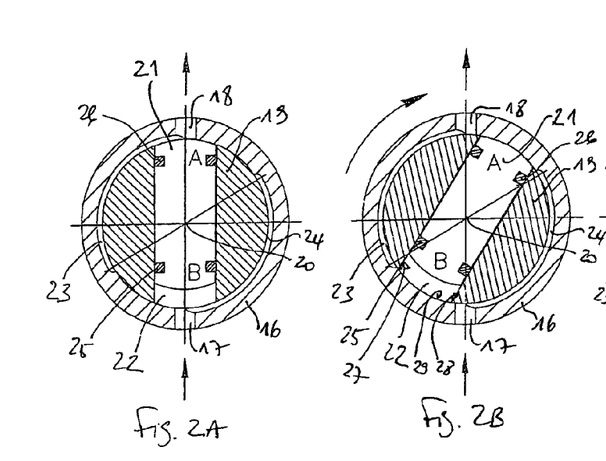

As shown in FIG. 2A, the liquid enters into a chamber 22 through inlet 17 in the body 16 and pushes the cylinder 21 upwards in the representation of FIG. 2A since the pressure at the inlet side 17 is higher than the pressure at the outlet 18 side. The liquid also fills the temporary chamber 23 and seals 25 and 26, for example O-rings, are provided on the piston 21.

In FIG. 2B, the cylinder 19 and the piston 21 are rotated clockwise around axis 20 in the body 16 of an angle of about 30° and the chamber 22 is now closed, delimited by the end B of the piston 21, the inner walls 27 and 28 of the cylinder and inner wall 29 of the body 16.

Figures 2C, 2D:
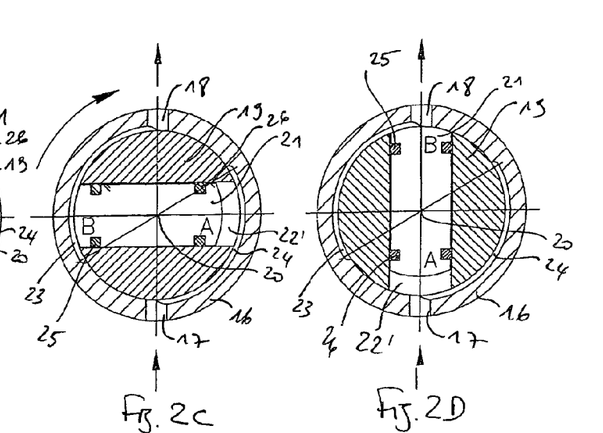

A further clockwise rotation of the cylinder 19 and the piston 21 of about 90° (value taken from the position of FIG. 2A) brings the system in the position represented in FIG. 2C. As can be understood when considering FIGS. 2B and 2C, clockwise rotation of the cylinder 19 and piston 21 from the position of FIG. 2B allows the temporary chamber 24 connected to inlet 17 to be connected to the end A of the piston 21, thus allowing the liquid under pressure in the inlet 17 to apply pressure against the 21 piston at its end A. Since the pressure at the inlet 17 is higher than the pressure at the outlet 18, the piston will move laterally in the direction of end B and the volume of the chamber 22 is diminished thus evacuating the liquid present through the outlet 18 and at the same time a chamber 22' is formed at the end A of the piston 21. This situation is represented in FIG. 2C.

Figures 2E, 2F, 2G, 2H:
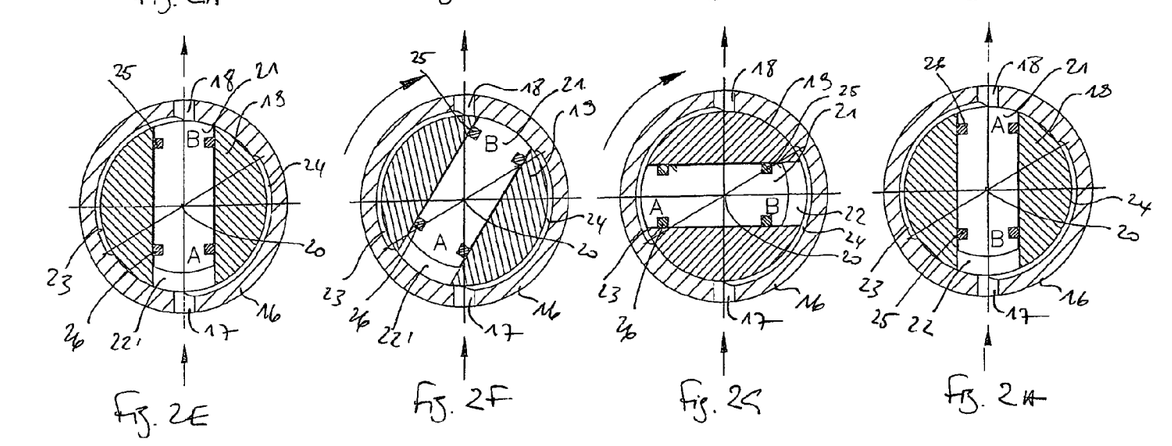

A further clockwise rotation of the cylinder 19 and the piston 21 of about 90° ends in the positioning represented in FIG. 2D, repeated in FIG. 2E which shows the same position of the elements.

Then, a new cycle may start as represented in FIGS. 2F to 2H, which is in fact similar to the cycle represented in FIGS. 2C to 2D and the description made above applies correspondingly. The only difference concerns the ends A and B of the piston, which are inverted.

The final position represented in FIG. 2H is identical to the position represented in FIG. 2A, the cylinder 19 having made a rotation of 360° as represented successively in the FIGS. 2A to 2H.

FIGS. 3 to 7 show another embodiment of the invention in which the temporary chambers are placed differently with respect to the first two embodiments.

Figure 3:
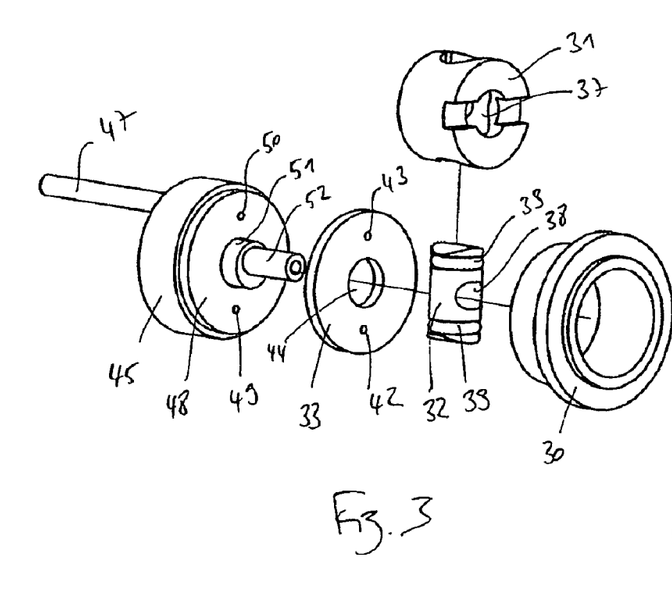
Figure 4:
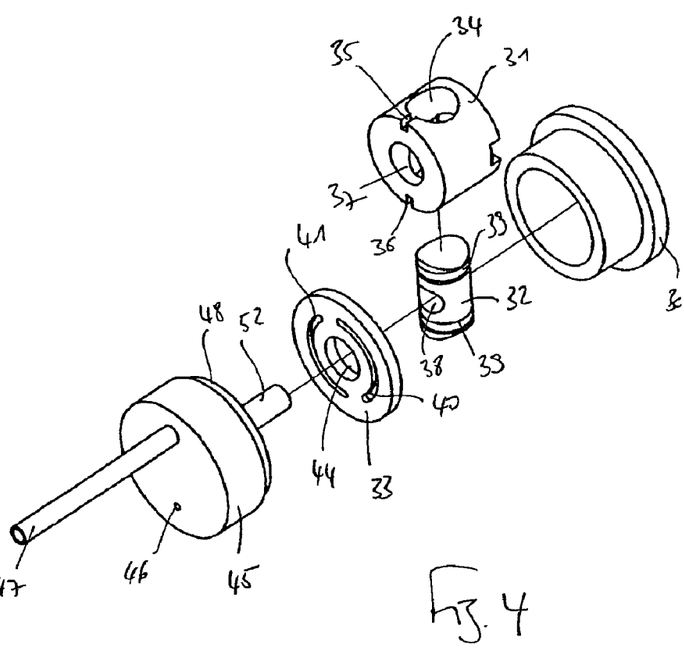

In FIGS. 3 and 4, a first perspective exploded view of this third embodiment is represented. This embodiment comprises a cage 30, a cylinder 31, a piston 32, and a first disc 33. The cylinder 31 in addition comprises a chamber 34 receiving the piston 32, two channels 35, 36 and an opening 37. The piston 32 also comprises an opening 38 and preferably two seals 39 such as O-rings.

The disc 33 further comprises two banana-shaped chambers 40, 41 on the side of the disc 33 opposite the piston and two openings 42, 43 which open on the piston side of the disc 33 and end inside the banana-shaped chambers 40, 41. Finally, the disc 33 also comprises a central opening 44.

Cage 30, cylinder 31 and disc 33 are attached together to form a first assembly, with the disc 33 and the cylinder relatively placed such that the openings 42, 43 of the disc are aligned with the channels 35, respectively 36 of the cylinder 31, and this assembly is rotated by a motor (not shown), the piston 32 moving perpendicularly to the axis of rotation of the assembly.

In a variant, it can be envisaged to form cylinder 31 and disc 33 in one single part rather than two separate parts, one criterion for choosing a construction in single part or in two separated parts may be the material used for the disc and for the piston.

Figure 6:
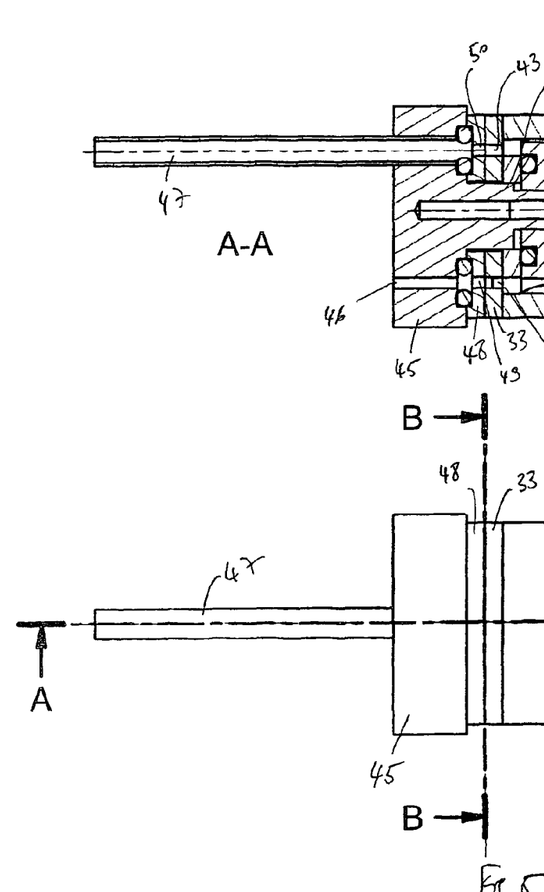
Figure 7:
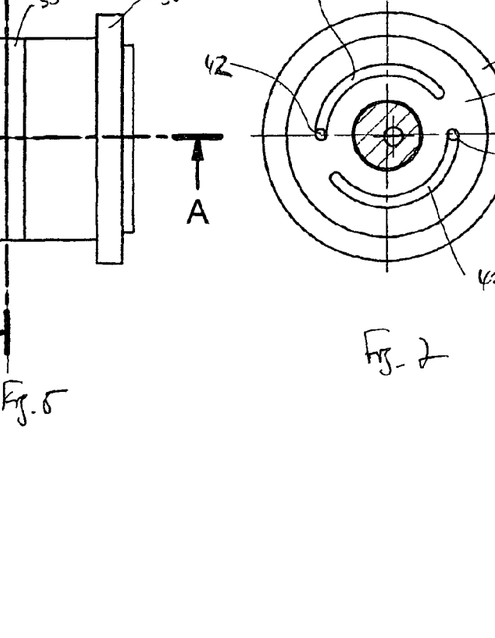

The pump also comprises a second assembly including a body 45 with an inlet 46 and an outlet 47 and carries a second disc 48. The second disc 48 comprises two openings 49, 50 which are connected to inlet 46, respectively outlet 47, and a first axis 51 which, when both assemblies are mounted together extends though the opening 44 of the disc 33 and the opening 37 of the cylinder 31. There is also a second axis 52, eccentrically disposed with respect to first axis 51, which extends though the opening 38 of the piston 32 when both assemblies are mounted together. This state is represented in FIGS. 5 to 7, FIG. 6 showing a cut view of the assembly along axis A-A of FIG. 5, whereas FIG. 7 illustrates a front view along axis B-B of FIG. 5, in which the same elements are identified by the same numerical references.

The system functions in the following manner. When the piston 32 is at full stroke, the openings 49 and 50 of disc 48 are between the two banana-shaped chambers 40 and 41 and there is no transfer of liquid. When the first assembly comprising cage 30, cylinder 31, piston 32 and disc 33 starts rotating relatively to second assembly comprising body 45, disc 48 with axis 51 and 52, the fact that the axis 51 and 52 are eccentric displaces the piston 32 laterally (for example downwards in FIG. 6) which consequently reduces the volume of the chamber 53. At the same time that the piston 32 moves, the openings 49 and 50 are connected to the banana-shaped chambers 40, 41 allowing liquid present in the chamber 53 to be transferred in a banana-shaped chamber 40 or 41 through channels 35 or 36. For the sake of clarity, let's assume it is banana-shaped chamber 40 that is filled by the liquid expelled from chamber 53 by the displacement of piston 32. This is thus done through channel 35 and opening 43. However, since the banana-shaped chamber is also connected to opening 50, the corresponding volume of liquid which is transferred from chamber 53 into banana-shaped chamber 40 by the displacement of the piston 32 is expelled through opening 50 and outlet 47.

At the same time, at the other end of the piston, an inverse behaviour takes place. While the volume of the chamber 53 (see FIG. 6) at one end of the piston 32 is reduced by the displacement of the piston 32, a chamber is formed at the other end of the piston 32 by its motion (see the principles exposed in relation to the embodiments of FIGS. 1A-1H and 2A-2H). This chamber is connected via channel 36 to the other banana-shaped chamber 41 through opening 42. Hence displacement of the piston to form a chamber will "aspirate" liquid present in banana-shaped chamber 41 and since this chamber is further connected to inlet 46 through opening 49, the banana-shaped chamber 41 will be filled by a corresponding volume of liquid taken from a reservoir.

As can be readily understood from the description above, each rotation of 180° will allow the system to expel a volume of liquid corresponding to the volume of the chamber 53 (see FIG. 6) and at the same time to fill a chamber with the same volume of liquid. It can also be easily understood that the volume of expelled fluid can be a function of the degree of rotation and through selectively stopping the rotation of piston 6 at intermediate positions during rotation. In this manner one may deliver volumes of fluid which are known fractions of the stroke volume expelled during a 180° rotation.

Interesting in this third embodiment is the use of discs, which, by relative rotation, allow the opening and the closing of the circuit. In addition, such discs have a large contact surface, which improves the leakproofness of the system.

The present invention can also be used to deliver drugs to other organs/tissues. One application is pain relieve drugs in the spine. A straightforward use might be in the delivery of intra-arterial chemotherapy in different malignancies. This approach seems particularly effective for liver (hepatocellular and metastatic colorectal) tumours, but also for uterine, gastric, head and neck and intracerebral malignancy. Drugs that could be administered by the present invention in this context might include cisplatin and fluorouracil. Other applications might include administration of vasodilators such as papaverine for recurrent cerebral vasospasm and the long-term administration of anti-fungal agents for particularly resistant infections.

As can be readily understood from the above description, the system according to the invention is rather simple. In addition, it is valveless which is a clear advantage over the known systems. There is also no fluidic communication between inlet and outlet so that even if the system is blocked, there is no risk that the reservoir empties itself in the body carrying the system.

Typically, the device can be made in plastic or metal (for example stainless steel) or a combination of both. The discs can be made of plastic, metal, silicon or ceramics. In a variant, as mentioned above, the disc 33 could be made integral with the cylinder 31.

Figure 8:
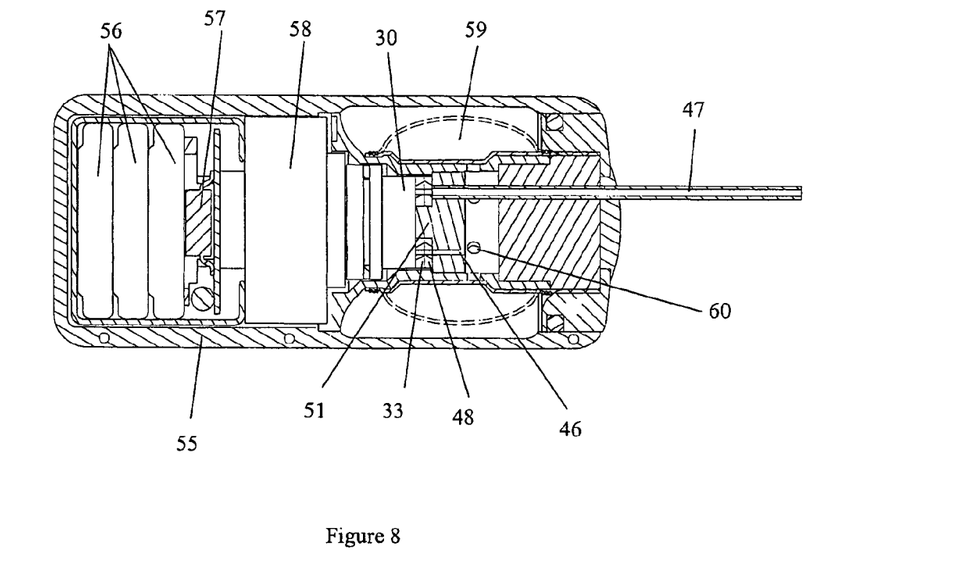
FIG. 8 shows a general cut view of a pump according to the present invention.

FIG. 8 shows in a schematical way a cut side view of a complete pump according to the third embodiment of the invention corresponding to FIGS. 3 to 7. The represented pump comprises an outer body 55 with batteries 56, an electronic circuit 57, a motor 58, the cage 30, the two disks 33 and 48, the inlet 46, the outlet 47 and the axis 51, as described with reference to FIGS. 3 to 7. Around the inlet 46, there is in addition a reservoir 59 in which the liquid to be delivered is maintained and the liquid can be introduced in said inlet 46 through opening 60. The representation of FIG. 8 is a schematical representation comprising the third embodiment disclosed above and the description of this embodiment with FIGS. 4 to 7 applies correspondingly. As said, this is only an example and the principles of the first and second embodiments can also be used in the assembled pump of FIG. 8 with corresponding modifications and adaptations.

Also, FIG. 8 represents a preferred embodiment in which the entire implantable system is embedded in the same body 55, including motor 58, energy source 56, electronic circuit 57 and reservoir 59. Of course it can be envisaged for different reasons (especially to reduce the size of the body 55) not to include all these elements in the same body. One element that could be removed is the energy source 56, when batteries are used: indeed batteries must be changed after a certain time and this operation would imply the removal of the implanted device. To overcome this specific problem, an external source may be used to transmit energy telemetrically or through other suitable means to the motor 58 and the circuit 57. Other variants are given at the end of the present description.

Figure 9A:
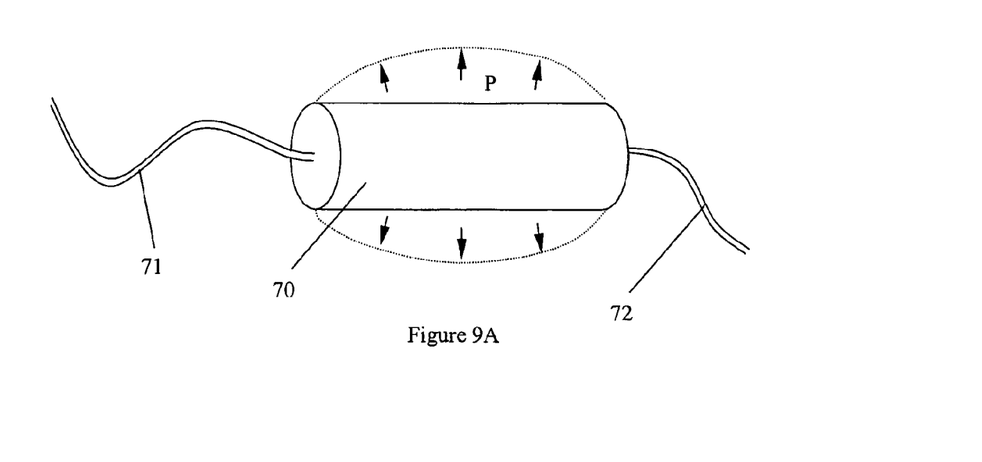
FIGS. 9A to 9C illustrate an example of a release chamber suitable for use in the system according to the present invention.

A non-limiting example of a delivery chamber that can be used in the present system is described with reference to FIGS. 9A to 9C.

A main feature of this delivery chamber is that it is elastically compliant therefore the pump fills the elastic chamber at each stroke with liquid. The elastic chamber recoil then brings the chamber back to its original volume and, by doing so, empties gradually the liquid at an outlet end of the chamber. The advantage of using such a chamber is the fact that the liquid is not delivered in one single stroke into the body carrying the system but rather is delivered slowly (depending on the characteristics of the chamber) over time.

Accordingly, the elastic delivery chamber 70 (FIG. 9A) comprises an inlet 71 connected to the pump (not shown in FIG. 9A) for example through the outlet 3 of FIGS. 1A to 1H, or 18 of FIGS. 2A to 2H, or 47 of FIGS. 3 to 6 and 8 and an outlet 71 in the shape of a catheter for the delivery of the liquid pumped into the chamber 70. By its compliancy, the chamber 70, when regaining its original volume, expels the liquid through outlet 72/catheter.

Figure 9B:
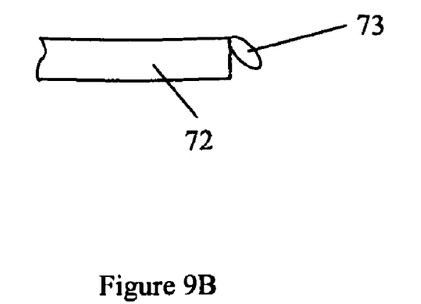
Figure 9C:
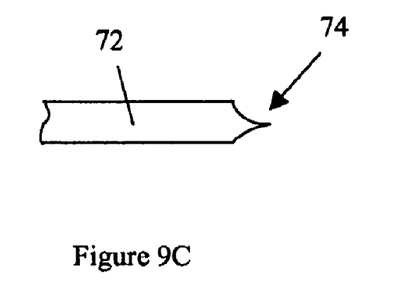

FIGS. 9B and 9C illustrate two exemplary ways of realizing the end of the catheter 72 with a backstop. In FIG. 9B, the backstop has the shape of a back flow stop valve 73 and in FIG. 9C a deformation 74 of the end of the catheter 72 is used to the same effect. These configurations keep the end of the catheter 72 closed, unless a positive pressure gradient created by the movement of piston 6 (see FIGS. 1A to 1H) or piston 21 (see FIGS. 2A to 2H) or piston 32 (see FIGS. 3 to 6) forces the catheter end to open so that the fluid is expelled. The closed catheter end serves in blocking cells, body fluids or tissues from entering the catheter, thereby provoking a clogging up of the conduit. Of course, other equivalent means can be envisaged for the same purpose.

In FIGS. 10A to 10D, several non-limiting examples of a liquid reservoir suitable for use in the present invention are disclosed. In particular, a feature that is sought for such reservoirs is a small size (especially when empty) to allow their insertion in a body through a trocar or similar device.

Figure 10A:
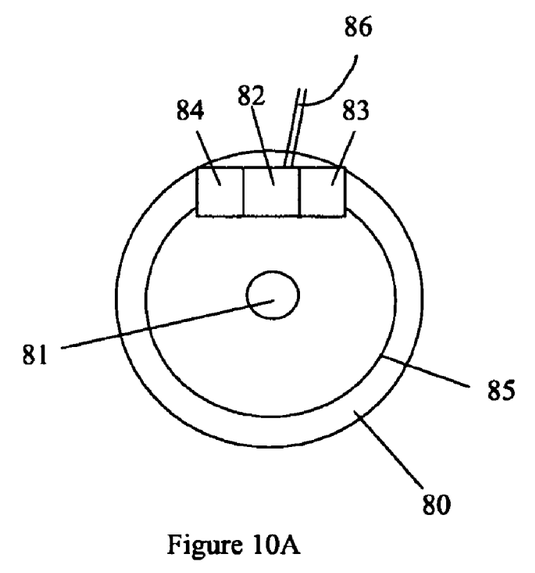
FIGS. 10A to 10D illustrate an example of a reservoir suitable for use in the system according to the present invention.

A first embodiment is illustrated in FIG. 10A, which shows a reservoir 80, with a septum 81 used to fill the reservoir from the outside, in a known fashion. A pump 82 (corresponding to the pump described above) is integrated in the reservoir 80. Further elements integrated in the reservoir are an electrical source 83 (for example batteries), an electronic device 84 used to control the system and an antenna 85 that is used for receiving instructions from outside, for example from a wireless emitter used by a doctor. This allows, for example a distance programming of the electronic device. An outlet catheter 86 is connected to the pump, for example corresponding to the inlet catheter 71 of FIGS. 9A to 9C to fill a delivery chamber as disclosed in these figures.

Figure 10B:
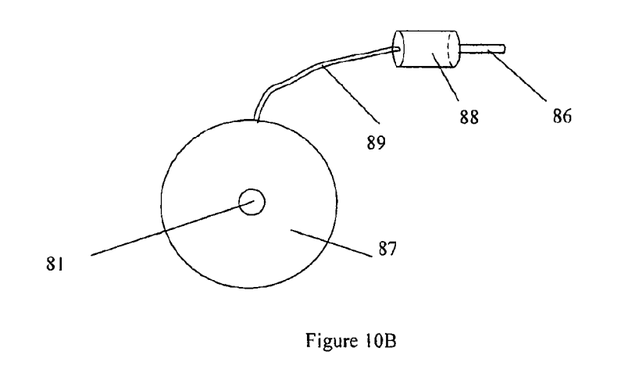

A second embodiment is represented in FIG. 10B. In this embodiment, the reservoir 87 still comprises a septum as the reservoir of FIG. 10A but the pump 88 with electrical source and electronic control means are not integrated in the reservoir 87. Rather, the pump 88 is connected to the reservoir via a feed catheter 89. On the outlet side of the pump 88, an outlet catheter 86 is connected, said outlet catheter corresponding, for example, to the inlet catheter 71 represented in FIGS. 9A to 9C to fill a delivery chamber as disclosed in these figures.

Figure 10C:
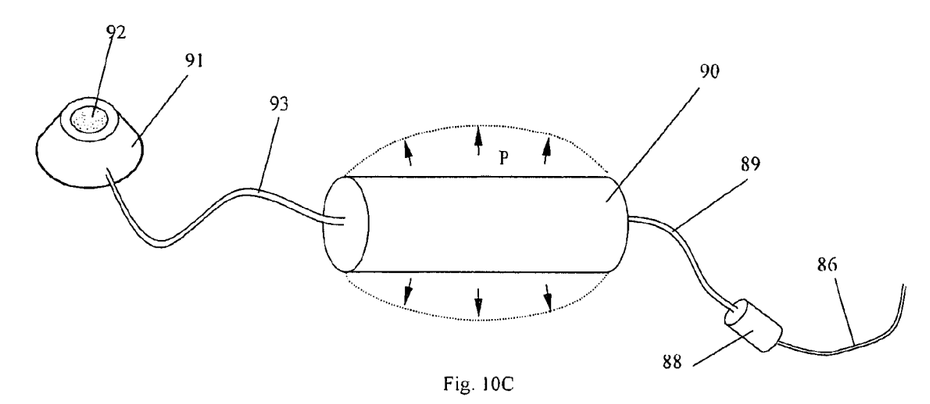

A third embodiment of a reservoir is illustrated in FIG. 10C. In this embodiment, the reservoir 90 has an elongated shape, so that it can be inserted in the human body through trocars. Part or the entire reservoir 90 is made of an inflatable material. Fluid or drug can be delivered into the reservoir via an access port 91, said access port carrying the septum 92 for the filling of the reservoir, such as those found commercially for cancer treatment or in adjustable gastric rings. Said liquid is introduced into the reservoir by transcutaneous injection into the port 91, said port been connected to the reservoir via a flexible feed catheter 93. When said liquid is introduced in the reservoir 90, said reservoir expands to accommodate the desired volume of liquid. This embodiment also uses a feed catheter 89 from the reservoir to the pump 88 and an outlet catheter 86, as in the preceding embodiments. In another form of execution, the access port 91 with its septum 92 are integrated into the inflatable reservoir 90, eliminating the need for the feed catheter 93.

In a variant, the reservoir 59 represented in FIG. 8 has the same features of expandability of the reservoir 90 of FIG. 10C. In this variant, the need for feed catheter 89 as represented between the reservoir 90 and the pump 88 in FIG. 10C is eliminated.

Figure 10D:
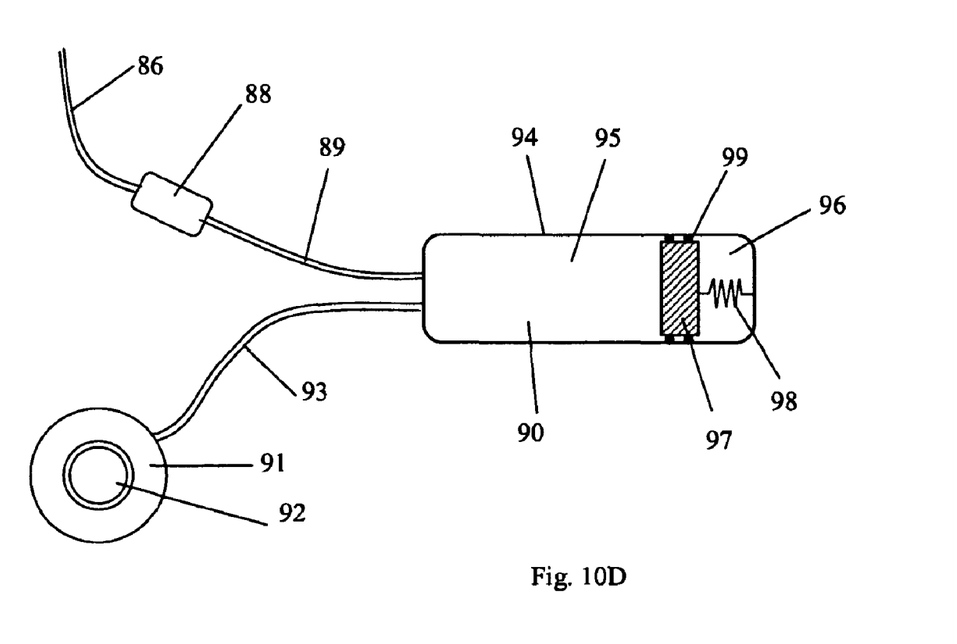

A fourth embodiment of a reservoir is illustrated in FIG. 10D. In this embodiment, the reservoir 90 has an elongated shape, so that it can be inserted in the human body through trocars. The outer shell of the reservoir 94 is rigid. The reservoir is separated into two variable volume parts 95 and 96 by a piston 97. The piston can slide within the reservoir in a leak-proof manner, as guaranteed by the choice of material and the quality of surface or by the addition of o-rings 99. The piston is connected to a spring 98, which in turn is connected to the wall of the reservoir 90. The spring 98 is always in compression, thus transferring via the piston a positive pressure on the fluid in the variable chamber 95. When said liquid is introduced in the reservoir 90, said variable chamber 95 expands by further compressing the spring 98 to accommodate the desired volume of liquid.

It will be understood that various modifications and/or improvements obvious to the person skilled in the art can be made to the embodiments described hereinabove without departing from the scope of the invention defined by the annexed claims.

For example, the principle of pressure differential used in the embodiment represented in FIGS. 2A to 2H can be applied to the embodiment represented in FIGS. 3 to 7 with corresponding results: a higher pressure at the inlet 46 would accordingly be used to displace the piston 32 and expel the fluid through the outlet 47. In such an embodiment, the axis 52 could be removed. Such higher pressure can be created by the use of reservoirs as described above which are elastically compliant and maintain a certain pressure on the liquid they contain.

In FIGS. 11A to 11D, a specific embodiment of an eccentric axis is represented in cut view, said axis corresponding to axis 7 of FIGS. 1A to 1H or axis 52 of FIGS. 3 to 7. As can be readily understood from the description above, and for example from FIG. 1B, in this position of the cylinder all the chambers are closed. However, the cylinder must be further rotated as shown in FIG. 1C, a rotation that is not possible if there is not play between the eccentric axis 7 and the opening of the piston in which it is received since the liquid can not be compressed.

To overcome this problem, there is the following alternative: either using relative play between the parts (in this case the eccentric axis and the opening of the piston) to avoid blockage of the system or defining a specific profile for the eccentric axis to avoid displacement of the piston in certain positions of the cylinder, while still rotating the cylinder.

The disadvantage of a play is of course the fact that it then renders the system less precise as regards the quantity of liquid effectively delivered.

Accordingly, it can be interesting to develop another solution, as shown in FIGS. 11A to 11D. This solution is based on the principle used for example for camshaft, in which the eccentric axis is not purely cylindrical but has a different peripheral shape as explained hereunder.

Figure 11A:
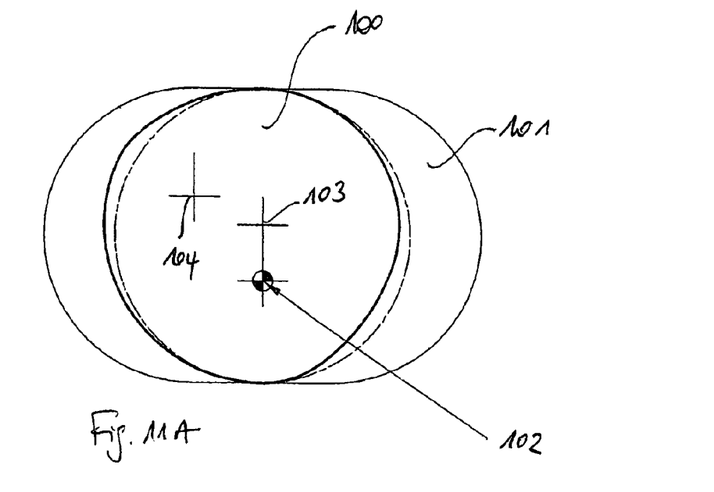
FIGS. 11A to 11D show a specific embodiment of an eccentric axis.

In FIG. 11A, there is represented an eccentric axis 100 (corresponding to axes 7 or 52), which is received in an opening 101 of the piston. Represented on the axis 100 are three centers of rotation, the center 102 being the center of rotation of the cylinder (corresponding to the axis 5 of FIGS. 1A to 1H for example), and a first offset center of rotation 103 and a second offset center of rotation 104.

Figure 11B:
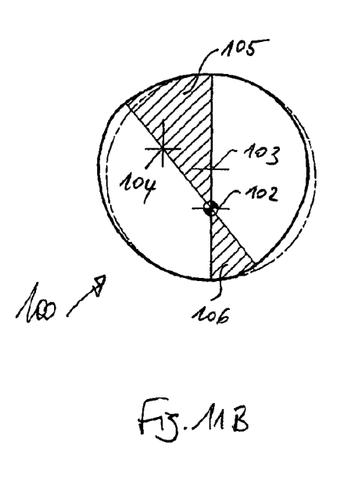

These centers of rotation allow to define different sectors of the axis 100 which have the same radius. In FIG. 11B, there are two sectors 105 and 106 with a constant radius which are defined around the centre of rotation 102.

Figure 11C:
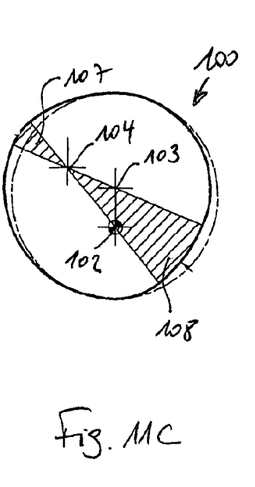

Then in FIG. 11C, there are two further sectors 107, 108 which are adjacent to the sectors 105/106 which have different radius and they are defined around offset center of rotation 104.

Figure 11D:
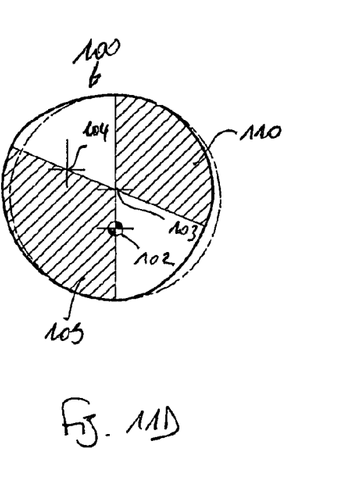

Finally in FIG. 11D, there are two more sectors 109, 110 which have another radius and are defined around offset center 103.

Is it understood that the sum of each radius (i.e. of sectors 105/106 or 107/108 or 109/110) is equal to the width of the opening 101 of the cylinder.

Of course, it is clear that the position of the different sectors with constant radius must be disposed appropriately relatively to the position of the chambers in the cylinder, in order to fulfil their aim.

The pump, in all the embodiments described above, may comprise a telemetry system, such as an RFID or Bluetooth module which would allow the pump to receive and also send signals and information to an external control unit. The external control unit may be used to program the implant function (i.e., drug release rates, time profile of bolus delivery, etc.) but it can also be used to collect functional data from the implant, such as history of doses, battery status, state of the good functioning of the device etc. The telemetry system may be also used to deliver energy to the implant, in a manner similar to other telemetrically energized implantable devices, for example such as those described in U.S. Pat. No. 5,820,589.

Further, the pump in all the embodiments described above, can be connected either physically or wirelessly to a physiological signal sensing system which would provide information as to the state of certain physiological variables (i.e. pressure, temperature, electrical activity, etc.). The signal can then be interpreted by the pump, for example by its calculating means (containing an appropriate program) and used to decide (based on imbedded decision algorithms) whether or not to deliver a therapeutic dose. One such concrete example would be the connection of a pump to a system measuring ECG or other brain activity signals, which then would allow the pump to deliver, when needed (for example based on predetermined parameters), drugs intracranially. Another example would be the use of the pump in heart failure patients where end diastolic pressure or volume is measured and this signal is used by the pump to deliver in the vena cava, systemically or directly to the heart cavities inotropic or other appropriate drug function regulating drugs. In a similar fashion, the pump can be coupled to an ECG measuring system and use this signals to decide when to deliver cardiac rhythm management drugs either in the vena cava or directly in the heart muscle or heart cavities.

For small animal applications, for intracranial, peripheral or other human applications it is essential that the pump is compact with a minimal weight and volume. One such example is given in FIG. 11. To further reduce weight and volume, it is also possible to remove batteries and to store energy in the implant during drug filling, by elastic deformation of a spring or membrane attached to the reservoir. This energy can be gradually released during emptying of the reservoir and be used accordingly to operate the motor. Energy storage can be also achieved by the natural human or animal motion, used a system similar to the automatic (battery-free) watches.

As can be readily understood from the above description, the system is preferably implanted through a trocar or similar device. Hence, the size (diameter) should not exceed certain values corresponding to the sizes of such devices. Typically, a maximal cross-sectional diameter would be of about 18 mm, but other sizes can be envisaged depending on the application and the location where the device is to be implanted.

REFERENCE NUMBERS 1 external body
2 inlet
3 outlet
4 cylinder
5 cylinder axis
6 piston
7 piston axis
8, 8' inlet chamber
9 first temporary chamber
10 second temporary chamber
11 seal
12 seal
13 inner wall of cylinder 4
14 inner wall of cylinder 4
15 inner wall of body 1
16 external body
17 inlet
18 outlet
19 cylinder
20 cylinder axis
21 piston
22,22' inlet chamber
23 first temporary chamber
24 second temporary chamber
25 seal
26 seal
27 inner wall of cylinder 21
28 inner wall of cylinder 21
29 inner wall of body 16
30 cage
31 cylinder
32 piston
33 first disc
34 chamber of cylinder 35 channel
36 channel
37 cylinder opening
38 piston opening
39 seals of piston
40 banana-shaped chamber
41 banana-shaped chamber
42 opening of disc
43 opening of disc
44 central opening
45 body
46 inlet
47 outlet
48 second disc
49 opening
50 opening
51 first axis
52 second axis
53 chamber in front of piston
54
55 outer body
56 batteries
57 electronic circuit
58 motor
59 fluid reservoir
60 opening
70 elastic delivery chamber
71 inlet of chamber 70
72 outlet of chamber 70
73 stop valve
74 deformation
80 reservoir (1$^{st}$ embodiment)
81 septum
82 pump
83 electrical source
84 electronic device
85 antenna
86 outlet of pump 82
87 reservoir (2$^{nd}$ embodiment)
88 pump
89 feed catheter
90 inflatable body
91 ring
92 septum of ring
100 eccentrical axis
101 opening
102 center of rotation of cylinder
103 first offset center of rotation
104 second offset center of rotation
105 first sector around center 102
106 second sector around center 102
107 first sector around center 104
108 second sector around center 104
109 first sector around center 103
110 second sector around center 103

The invention claimed is:

1. An implantable delivery device comprising at least
a body,
an inlet,
an outlet, and
actuating means,
wherein the actuating means comprise at least an actuator displacing a piston in a rotating cylinder forming at least one variable volume chamber, the volume of which is varied by rotation of said cylinder thereby pumping liquid such as a drug from a reservoir through said inlet and expelling said pumped liquid from said variable volume chamber through at least a first temporary chamber and said outlet by variation of said volume,
wherein the delivery device is an implantable delivery device, and
wherein the actuating means comprise an eccentric system in which the cylinder rotates around a first axis and the piston rotates around a second axis both said axes being coaxial and laterally offset.

2. The device as claimed in claim 1, wherein said temporary chamber is situated between said cylinder and said piston.

3. The device as claimed in claim 1, wherein said temporary chamber is over said piston.

4. The device as claimed in claim 1, wherein the device comprises two temporary chambers.

5. The device as claimed in claim 4, wherein the device comprises a first disk in which said temporary chambers are formed, said disc being attached to said cylinder.

6. The device as claimed in claim 5, wherein the device comprises a second disc with two openings being connected to said inlet and said outlet, said first disc rotating with respect to said second disc.

7. The device as claimed in claim 6, wherein said discs are made of metal, plastic, silicon or ceramics.

8. The device as claimed in claim 1, wherein the device comprises a variable volume chamber at each end of the piston.

9. The device as defined in claim 1, wherein the piston comprises at least one seal.

10. The device as claimed in claim 1, wherein said second axis is not cylindrical and has sectors with different radius.

11. The device as claimed in claim 1, wherein the actuator is realized by pressure, in such a way that the pressure of the liquid in said inlet is higher than the pressure of the liquid in said outlet thereby displacing said piston by this pressure differential.

12. The device as claimed in claim 1, wherein the actuating means comprise a motor linked to an energy source and calculating means.

13. The device as defined in claim 12, wherein the motor and/or the energy source and/or the calculating means are inside said device.

14. The device as defined in claim 13, wherein the energy source is outside the device, the motor is inside the device and energy is transmitted telemetrically to the motor.

15. The device as defined in claim 12, wherein the motor and/or the energy source and/or the calculating means are outside said device.

16. The device as claimed in claim 12, wherein the device is able through its calculating means to decide to deliver a therapeutic dose on the basis of predetermined parameters delivered by a sensing system.

17. The device as defined in claim 16, wherein said parameters are physiological parameters.

18. The device as defined in claim 16, wherein the delivery by the sensing system to the calculating means is made wirelessly or via a physical connection.

19. A delivery chamber for a device as defined in claim 1, wherein the chamber comprises at least an elastically compliant chamber, an inlet catheter and an outlet catheter connected to said chamber.

20. A delivery chamber as defined in claim 19, wherein the outlet catheter comprises a stop valve.

21. A delivery chamber as defined in claim 20, wherein the stop valve has the shape of a deformation.

22. A drug delivery system that can be implanted through a trocar, wherein the system comprises at least a delivery chamber as defined in claim 19.

23. A reservoir for a device as defined in claim 1, wherein the reservoir cooperates with a septum used to fill said reservoir.

24. A reservoir as defined in claim 23, wherein the reservoir is elastically compliant.

25. A reservoir as defined in claim 23, wherein said reservoir contains a piston cooperating with a spring, said piston delimiting two variable volume parts in said reservoir, said spring being in compression in order to transfer via the piston a positive pressure on the fluid present in one of said variable chamber.

26. A reservoir as defined in claim 23, wherein the reservoir cooperates with a delivery device through a catheter.

27. A drug delivery system that can be implanted through a trocar, wherein the system comprises at least a reservoir as defined in claim 23.

28. A system comprising a device as defined in claim 1, a delivery chamber, and a reservoir.

29. A drug delivery system that can be implanted through a trocar, wherein the system comprises at least a device as defined in claim 1.

* * * * *